United States Patent
Côté

(10) Patent No.: US 11,471,313 B2
(45) Date of Patent: Oct. 18, 2022

(54) ANKLE FOOT ORTHOSIS

(71) Applicant: ORTHÈSES TURBOMED INC. / TURBOMED ORTHOTICS INC., Saint-Augustin-de-Desmaures (CA)

(72) Inventor: François Côté, Lévis (CA)

(73) Assignee: Orthèses Turbomed inc. / Turbomed Orthotics inc., Saint-Augustin-de-Desmaures (CA)

( * ) Notice: Subject to any disclaimer, the term of this patent is extended or adjusted under 35 U.S.C. 154(b) by 105 days.

(21) Appl. No.: 16/631,286

(22) PCT Filed: Sep. 4, 2018

(86) PCT No.: PCT/CA2018/051062
§ 371 (c)(1),
(2) Date: Jan. 15, 2020

(87) PCT Pub. No.: WO2019/046932
PCT Pub. Date: Mar. 14, 2019

(65) Prior Publication Data
US 2020/0206008 A1 Jul. 2, 2020

Related U.S. Application Data

(60) Provisional application No. 62/554,147, filed on Sep. 5, 2017.

(51) Int. Cl.
*A61F 5/14* (2022.01)
*A61F 5/01* (2006.01)

(52) U.S. Cl.
CPC ................... *A61F 5/0113* (2013.01)

(58) Field of Classification Search
CPC .... A61F 5/0113; A61F 5/0127; A61F 5/0111; A61H 3/00; A63B 23/10
(Continued)

(56) References Cited

U.S. PATENT DOCUMENTS

| 4,459,980 A * | 7/1984 | Perser | A61F 5/0113 602/27 |
| 7,766,851 B2 * | 8/2010 | Lindh | A61F 5/0113 602/27 |

(Continued)

FOREIGN PATENT DOCUMENTS

| FR | 2832923 A1 | 6/2003 |
| GB | 117877 A | 8/1918 |

(Continued)

OTHER PUBLICATIONS

Turbo Med Orthotics—The Most Advanced Foot Drop Brace, https://turbomedorthotics.com/ (retrieved on Internet Sep. 5, 2017).

*Primary Examiner* — Camtu T Nguyen
(74) *Attorney, Agent, or Firm* — Alexandre Daoust; Norton Rose Fulbright Canada LP

(57) ABSTRACT

The ankle foot orthosis has a foot section securable externally to a footwear worn by a user, a leg section having a leg engagement portion extending in front of the user's lower leg and being securable against a shin area of the user's lower leg, and two arm portions extending downwardly from the leg engagement portion, on opposite sides of the user's lower leg, and a hinge section having two hinge members disposed on opposite sides of the user's ankle, each hinge member having two ends being elastically stretchable away from one another, with a first one of the ends being secured to a corresponding one of the leg arm portions, and a second one of the two ends being secured to the foot section, with a spacing between the hinge members and the arm portions forming a foot engagement path allowing the user to respectively engage or disengage his foot from the footwear across the spacing.

15 Claims, 3 Drawing Sheets

(58) Field of Classification Search
USPC .......................................................... 602/28
See application file for complete search history.

(56) References Cited

U.S. PATENT DOCUMENTS

| | | |
|---|---|---|
| 8,529,484 B2 | 9/2013 | Savard |
| 2005/0038365 A1 | 2/2005 | Scott |
| 2011/0196277 A1* | 8/2011 | Savard ................. A61F 5/0127 602/28 |

FOREIGN PATENT DOCUMENTS

| | | |
|---|---|---|
| GB | 1315590 A | 5/1973 |
| WO | 2005097014 | 10/2005 |
| WO | 2007106017 A1 | 9/2007 |
| WO | 2017024382 A1 | 2/2017 |

* cited by examiner

ANKLE FOOT ORTHOSIS

FIELD

The improvements generally relate to the field of orthosis, and more specifically to ankle foot orthosis adapted to address foot drop.

BACKGROUND

Foot drop (sometimes alternately referred to as drop foot or foot dangle) is the condition of a person who is unable to suitably lift his or her foot—that is, unable to perform the dorsal flexion (dorsiflexion) motion. The exact cause of foot drop can vary, ranging from weakness, irritation or damage of nerves or muscle paralysis, for instance. Foot drop makes walking difficult as the toes tend to drag on the ground which leads to tripping and instability. Persons suffering from foot drop typically adapt by using their hip muscles to exaggerate lifting the foot above the ground (known as a "steppage gait") or by swinging their leg outward so that the foot can clear the ground (known as "circumduction").

Many ankle foot orthosis had been proposed to address this condition in the past, to avoid gait irregularities stemming therefrom and/or otherwise limiting the impact of this condition on person's daily lives. However, these ankle foot orthosis had various inconveniences. The most common inconvenience was caused by the fact that these orthosis configurations were intended to extend within the footwear, more specifically between the foot and the sole, and had a structural member engaged against the person's foot or ankle which was known to cause irritation, thus severely hindering the amount of time the brace could be used and the nature of the activities for which the brace was considered suitable. This can be particularly problematic when foot drop is associated with loss of sensation, in which case the irritation or damage caused by the brace to the person's foot or leg will not immediately be perceived, and perhaps not noticed before significant damage to the person's foot or ankle has occurred.

Turbomed Orthotics developed the FS 3000 ankle foot orthosis (see http://turbomedorthotics.com/) which has been widely acclaimed since its commercial release. More details about the functionality of the FS 3000 ankle foot orthosis is presented in U.S. Pat. No. 8,529,484. This ankle foot orthosis is secured externally to the person's footwear, and can be suitable for prolonged and/or intensive use. However, there always remains room for improvement.

SUMMARY

In accordance with one aspect, there is provided an ankle foot orthosis comprising a foot section securable externally to a footwear worn by a user, a leg section having a leg engagement portion extending in front of the user's lower leg and being securable against a shin area of the user's lower leg, and two arm portions extending downwardly from the leg engagement portion, on opposite sides of the user's lower leg, and a hinge section having two hinge members disposed on opposite sides of the user's ankle, each hinge member having two ends being elastically stretchable away from one another, with a first one of the ends being secured to a corresponding one of the leg arm portions, and a second one of the two ends being secured to the foot section, with a spacing between the hinge members and the arm portions forming a foot engagement path allowing the user to respectively engage or disengage his foot from the footwear across the spacing.

Many further features and combinations thereof concerning the present improvements will appear to those skilled in the art following a reading of the instant disclosure.

DESCRIPTION OF THE FIGURES

In the figures.

DETAILED DESCRIPTION

Figure 1:
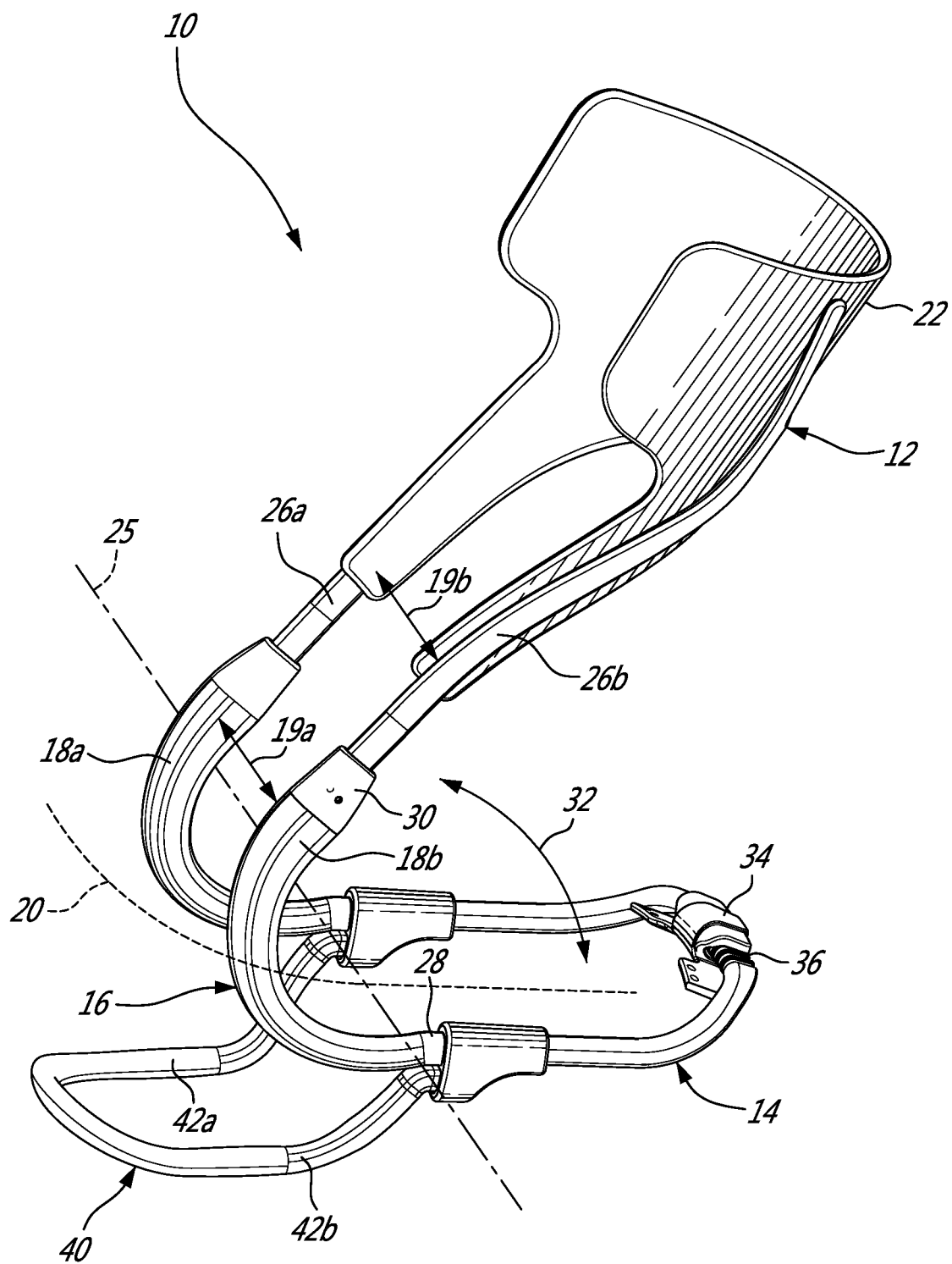
FIG. 1 is an oblique view of an example of a an ankle foot orthosis, in accordance with an embodiment.

While the FS 3000 is particularly well suited for patients suffering only from the foot drop condition, there remained an inconvenience with the FS 3000 ankle foot orthosis which limited its usability for a certain category of patients. More specifically, some patients suffer not only from foot drop, but also suffer from additional physical limitations. For instance, some patients may have partial hand paralysis in addition to foot drop, and may therefore require assistance to install and remove the FS 3000 ankle foot orthosis from their foot and leg, which can be acceptable, though undesirable. More specifically, the FS 3000 ankle foot orthosis has a leg section extending upwardly behind the wearer's leg/against the calf muscle, a foot section secured to the front and the rear of the footwear, and an elastically-flexible hinge section connecting the foot section to the leg section. The main purpose of the elastically-flexible hinge section is to provide the restoring foot-lifting force (dorsiflexion) to bias the foot to its lifted position, by acting between the leg section and the foot section.

In practice, in the FS 3000 model, the elastically-flexible hinge section is pre-loaded, meaning that the elastically-flexible hinge section is stretched from its relaxed state when worn by a user, and maintained in that stretched state during normal use, thereby permanently exerting an upward lifting force on the foot around the ankle, biasing the foot in a raised position (pivoting the toes around the ankle, towards the lower leg/shin—dorsiflexion). When the user moves his foot downwardly (plantar flexion or plantarflexion), additional elastic load is accumulated in the hinge section, and releasing the downward force exerted by the user allows the brace to return to its intermediate, pre-loaded state of tension, returning the foot to its upwardly raised stated. Moreover, the leg section extends behind the person's lower leg and against the calf muscle.

Accordingly, some amount of flexibility and strength is required from the user to install the brace to his/her foot. More specifically, strength is required from the arms/hands of the user to pivot the leg section away from the foot section into the "pre-tensioned" state, and flexibility is required due to position in which the user is when performing this action, which corresponds generally to the position of someone putting shoes on (which may be more inconvenient than, say, flexing the orthosis into its pre-loaded state on a workbench). It will be noted that this pre-loading force is exerted simultaneously to the movement of putting the footwear on, given the fact that the leg section extends behind the lower leg. While this action was considered suitable by persons having normal health, strength, and flexibility apart from the foot drop condition, it was considered difficult to perform for some persons suffering from additional disabilities, such as partial hand or arm paralysis. It will be noted that foot drop and partial hand or arm paralysis on the same side of the body is a relatively common lingering condition of persons having previously suffered from a cerebrovascular stroke.

Turning now to FIG. 1, an example of an ankle-foot orthosis 10 is presented. The ankle foot orthosis 10 has a leg section 12 connected to a foot section 14 by a hinge section 16. The hinge section 16 includes two arch-like, C-shaped members 18a, 18b which are spaced-apart from one another by a foot spacing 19a, forming a foot engagement/disengagement path 20 leading rearwardly and upwardly from the footwear 21 between the two C-shaped members 18a, 18b. The leg section 12 has a leg engagement portion 22 designed to be engaged against the front of a person's leg 24 (against the shin). The leg section also has two leg arm portions 26a, 26b, each extending downwardly from the leg engagement portion 22 on a corresponding side of the leg 24 and each being connected to a corresponding one of the C-shaped members 18a, 18b. The spacing 19b between the two leg arm portions 26a, 26b is continuous with the spacing 19a between the C-shaped members 18a, 18b, and contributes to the foot engagement/disengagement path 20. The foot section 14 can be secured to the other end 28 of C-shaped members 18a, 18b (opposite the ends 30 connected to the leg section 12. The foot section 14 can be based on the FS 3000 model, for instance, and be secured externally to the footwear 21. In an alternate embodiment, the foot section 14 can extend internally to the footwear, or be integrated as part of the footwear, for instance. The C-shaped members 18a, 18b are designed to elastically flex in a manner to allow stretching the opposite two ends 28, 30 of each C-shape member away from one another (elastic flexion movement 32 shown in FIG. 1) by accumulating elastic load therein, the elastic load biasing the wearer's foot upwardly in a dorsiflexion force during use.

Figure 2:
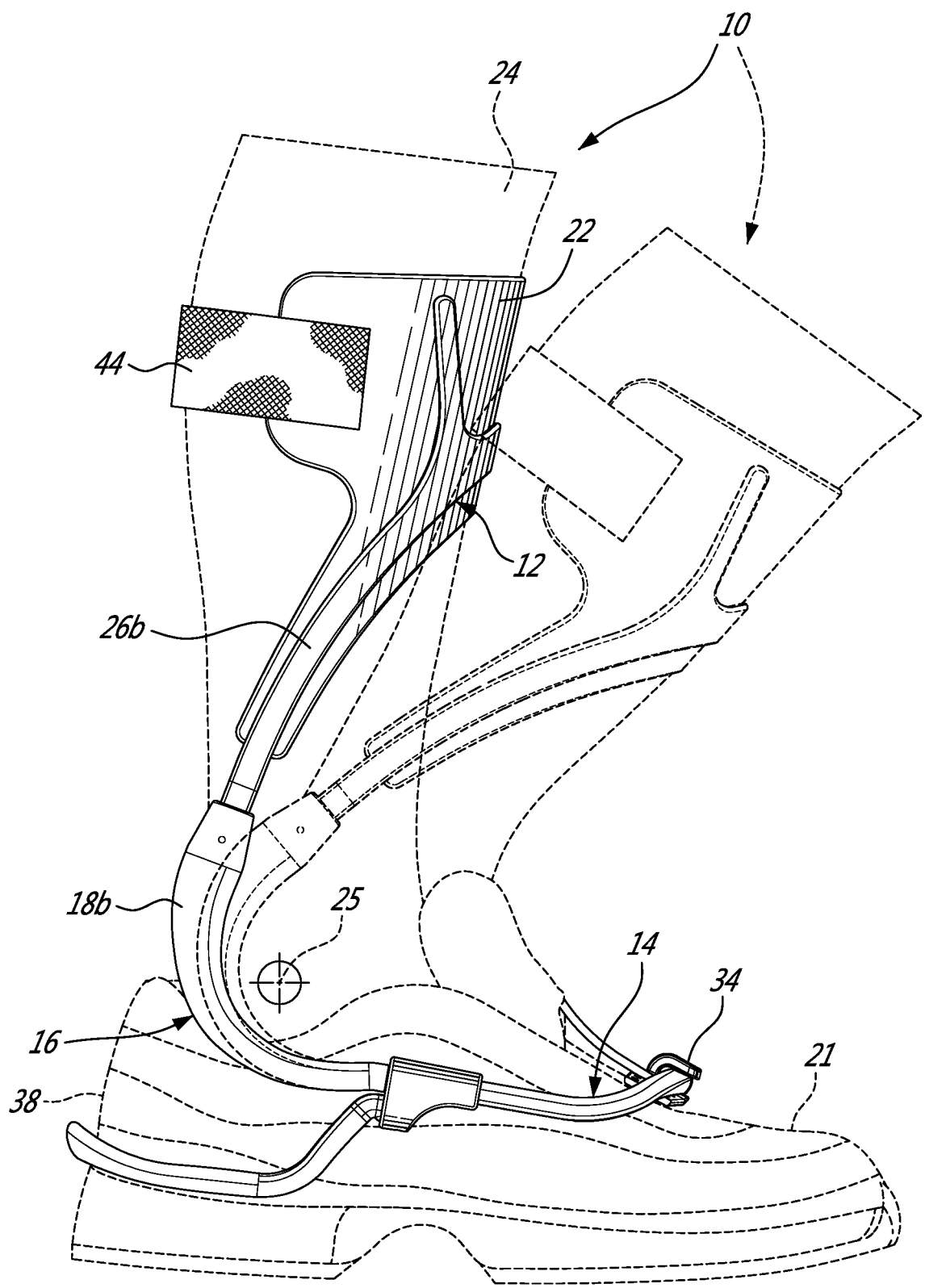
FIG. 2 is a side elevation view of the ankle foot orthosis of FIG. 1, secured to a footwear, and worn by a user.
Figure 3:
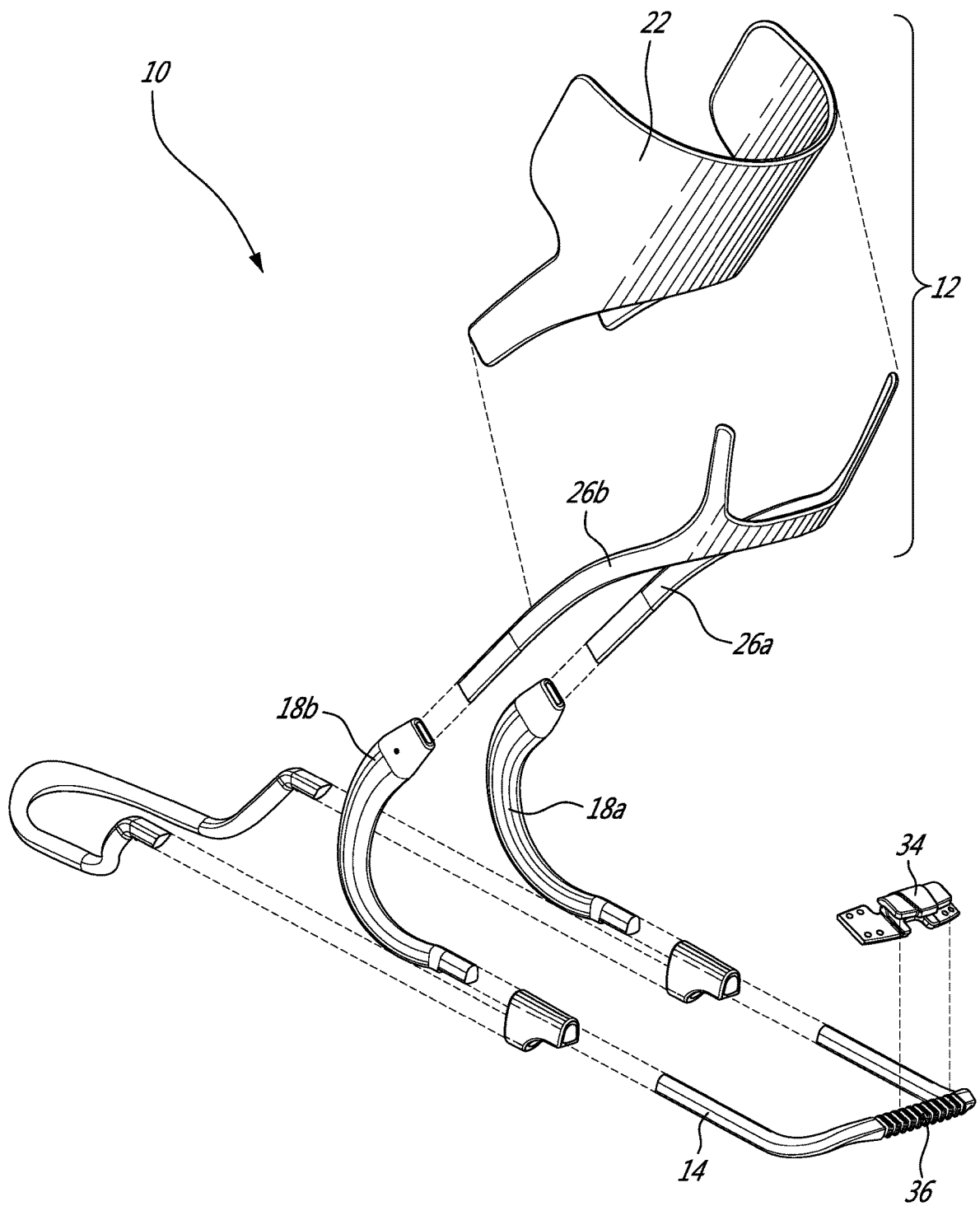
FIG. 3 is an exploded view of the ankle foot orthosis of FIG. 1.

In FIG. 1, the ankle foot orthosis 10 is shown in a relaxed state. FIG. 2 shows the ankle foot orthosis 10 secured to a user's footwear 21 and leg 24, in the intermediate, pre-loaded state. One can appreciate the difference in the angle between the leg portion 12 and the foot portion 14 between FIGS. 1 and 2, between which the foot section and the leg section were pivoted away from one another around the ankle pivot axis 25.

In one embodiment, the footwear 21 can be secured semi-permanently to the ankle foot orthosis, and can be considered to form part of the orthosis system. In this context, semi-permanent refers to the fact that the footwear 21 can typically remain integral with the ankle foot orthosis 10 when the user has removed his foot and leg therefrom, but the user can also de-attach the ankle foot orthosis 10 from the footwear 21 and re-attach it to another footwear. This latter functionality can be practical for re-using the ankle foot orthosis 10 with a new shoe once the former one has become worn, or using the same ankle foot orthosis 10 with different types of footwear, for instance (e.g. moving it to hiking boots for hiking and reverting to regular running shoes for everyday use thereafter).

The first step to wearing the ankle foot orthosis 10 can thus be to secure the footwear 21 to the foot section 14. This can be performed by a) securing an attachment bracket 34 to the footwear 21 (see FIG. 2—this can be done with laces or tie wraps, for instance), and then b) clipping the attachment bracket 34 (with the footwear 21 mounted thereon) to the attachment portion 36 of the foot section 14 (as shown in FIG. 1), and securing the heel portion 38 of the footwear 21 firmly between the two heel holding arms 42a, 42b of the heel portion 40 of the foot section 14 (into the configuration shown in FIG. 2). It will be noted here that this embodiment includes two heel holding arms 42a and 42b connected to one another behind the footwear 21, but other configurations are possible in alternate embodiments.

The second step to wearing the ankle foot orthosis 10 can then be to move the foot along the foot engagement path 20, between the leg arm portions 26a, 26b and C-shaped members 18a, 18b, and into the footwear 21. The person can then secure the footwear to his or her foot in a natural manner. At this stage, the hinge section 16 will remain unloaded, and the leg engagement portion 12 will remain inclined forwardly from the user's leg (shown in dashed lines in FIG. 2).

Once the user's foot is correctly engaged with the footwear 21, a third step can then be to, while holding the foot firmly against the ground, pull the leg engagement portion 12 backwards towards and against the user's shin 24, and then strap the leg engagement portion 12 snugly against the user's shin 24 using the strap 44, as shown in FIG. 2.

It will be understood from the above that the presence of the foot engagement path 20 extending between the two arms of the leg section/hinge members allows the user to engage his foot into the footwear 21 from behind, thereby dissociating the foot loading operation from the pre-loading operation. This can allow some users suffering from conditions which made self-attachment of the FS 3000 ankle foot orthosis difficult or impossible, to more easily attach the ankle foot orthosis themselves using an ankle foot orthosis such as shown in FIG. 1.

It will be understood that during use of the ankle foot orthosis, relatively complex dynamic mechanics come into play in making the ankle foot orthosis practical, comfortable, and functional. The fact that in this ankle foot orthosis configuration, the foot engagement path must be free from structural members, poses certain design challenges to maintain this functionality. In particular, in this configuration, it was found that the ankle foot orthosis performed better when the leg section was rigid, in the sense that the degree of elasticity allowing the ends of the arm portions to be stretched away from one another or bent laterally, or allowing the leg engagement portion to be twisted/rotated relative to the ends of the arm portions, or even allowing the arm portions to bend rearwardly or forwardly along their length, is preferably limited. Similarly, the configuration of the foot section can be selected in a manner to reduce the ability of the ends of the hinge members which are connected thereto to be stretched apart from one another, twisted/rotated relatively to the foot engagement portion, or even to limit the flexibility of the arms of the foot engagement portion along their length.

In this embodiment, the rigidity of the leg section was addressed by making the leg section of a material which was significantly more rigid (less elastic) than the hinge members. For instance, the leg section can have a structure made of stainless steel or carbon having an appropriate structural shape and thickness, whereas the hinge members can be made of plastic. Concerning the structural shape, it may be preferred for practical reasons to make the arm portions flat, although it will be understood that in alternate embodiments, using a T-shaped cross-section may significantly improve lateral rigidity for a given material thickness or quantity. Moreover, while it may be practical to have the leg engagement portion extend relatively high along the lower leg, thereby providing a greater lever for hinge flexion, it may be preferred to have a structural member connect the two arm portions relatively lower along the lower leg, to form an arch-like structure therewith and limit the extent to which the two arm portions can be stretched apart from one another. In practice, it can be preferred to leave the front of the foot at the height of the ankle free from any structural member for comfort and satisfactory operability, but a transversal structural member interconnecting the arm members can nonetheless be provided lower down the user's lower leg than the strap which engages the calf muscle. In this embodiment, this was achieved by prolonging structural members upwardly from the transversal structural member. A padded member was secured to the structural members of the leg engagement portion for comfort, and the padded member was secured to the user's lower leg using the strap.

As can be understood, the examples described above and illustrated are intended to be exemplary only. For instance, in alternate embodiments, different configurations of foot sections can be used. Moreover, different configurations of hinge sections can be used, such as spring and pivot assemblies instead of flexible plastic members for instance, while allowing the foot engagement path to be free from interference at the time of installing the orthosis. Moreover, different configurations of leg sections can be used, such as providing a transversal member lower along the user's lower leg, or a combination of two transversal members vertically interspaced from one another. The scope is indicated by the appended claims.

What is claimed is:

1. An ankle foot orthosis adapted to be worn by a user in a configuration of use, the user having lower leg, an ankle and a foot, the lower leg having a shin area, the ankle foot orthosis comprising;
   a foot section securable externally to a footwear, the footwear adapted to be worn by the foot of the user during use, the foot section having an anterior section adapted to be affixed above a toe portion of the footwear, and a posterior section adapted to engage a heel portion of the footwear;
   a leg section having a leg engagement portion adapted to be secured against the shin area of the user's lower leg during use;
   two arm portions adapted to extend downwardly from the leg engagement portion on opposite sides of the user's lower leg during use, the two arm portions permanently coupled to one another by the leg engagement portion, the two arm portions being separated from one another by an arm portion space;
   two hinge members, each hinge member adapted to be disposed on a corresponding, opposite side of the user's ankle during use, each hinge member having a first end and a second end, the first end and the second end being elastically stretchable away from one another, with the first end being secured to a corresponding one of the two arm portions, and the second end being secured to the foot section, the two hinge members being separated from one another by a hinge member space, the hinge member space communicating with the arm portion space and forming a foot engagement path;
   wherein the foot engagement path is adapted to allow the footwear to receive the foot across the hinge member space and into the configuration of use, and wherein the elastic stretchability of the two hinge members is adapted to bias the foot upwardly when in the configuration of use.

2. The ankle foot orthosis of claim 1 wherein the leg section and the foot section are made of stainless steel or carbon, and the two hinge members are made of plastic.

3. The ankle foot orthosis of claim 1 wherein each one of the two hinge members includes a C-shaped member made of an elastic material and extending between the first end and the second end.

4. The ankle foot orthosis of claim 1 wherein the hinge members are adapted to be in a pre-loaded state when in the configuration of use.

5. The ankle foot orthosis of claim 1 wherein the foot section includes two foot section arms, each foot section arm extending from a corresponding end of a corresponding hinge member to a distal end, and an interconnection member interconnecting the distal ends of the two foot section arms.

6. The ankle foot orthosis of claim 5 further comprising a footwear attachment bracket securable to the footwear, the footwear attachment bracket snappingly engageable with the interconnection member.

7. The ankle foot orthosis of claim 5 wherein the foot section further includes two rear arms each extending from a corresponding end of a corresponding hinge member to a distal rear end, and a rear interconnection member adapted to interconnect the two distal rear ends behind a heel section of the footwear.

8. The ankle foot orthosis of claim 1 wherein the hinge members are adapted to be in an unloaded state when not in the configuration of use, during which the first end and second end are inclined towards one another such that the leg section and the foot section form an angle below 90 degrees there between.

9. The ankle foot orthosis of claim 1 wherein the foot engagement path extends rearwardly and upwardly from the footwear.

10. The ankle foot orthosis of claim 1 wherein the first end faces the toe portion of the footwear wherein the second end faces the shin area of the user's lower leg.

11. The ankle foot orthosis of claim 1 wherein the leg section is made of stainless steel.

12. The ankle foot orthosis of claim 1 wherein the leg section is made of carbon.

13. The ankle foot orthosis of claim 1 wherein the hinge member is made of plastic.

14. The ankle foot orthosis of claim 1 wherein a transversal structural member permanently couples the two arm portions.

15. The ankle foot orthosis of claim 1 wherein the leg section comprises a padded member secured to the leg engagement portion and the padded member is securable against the user's lower leg using a strap.

* * * * *